United States Patent
Vaisberg et al.

(10) Patent No.: US 7,218,764 B2
(45) Date of Patent: May 15, 2007

(54) PLOIDY CLASSIFICATION METHOD

(75) Inventors: Eugeni A. Vaisberg, Foster City, CA (US); Daniel A. Coleman, San Mateo, CA (US)

(73) Assignee: Cytokinetics, Inc., San Francisco, CA (US)

( * ) Notice: Subject to any disclaimer, the term of this patent is extended or adjusted under 35 U.S.C. 154(b) by 131 days.

(21) Appl. No.: 11/097,451

(22) Filed: Apr. 1, 2005

(65) Prior Publication Data

US 2005/0272073 A1 Dec. 8, 2005

Related U.S. Application Data

(63) Continuation-in-part of application No. 09/729,754, filed on Dec. 4, 2000, now Pat. No. 6,876,760.

(60) Provisional application No. 60/588,640, filed on Jul. 15, 2004.

(51) Int. Cl.
  *G06K 9/00* (2006.01)
(52) U.S. Cl. .......................................... 382/129; 435/6
(58) Field of Classification Search ........ 382/128–134; 424/1.43, 801; 800/25; 536/23.1, 24.3; 435/4, 6, 9, 4.1, 7.24, 69.1, 91.4, 172, 333, 435/477

See application file for complete search history.

(56) References Cited

U.S. PATENT DOCUMENTS

| | | | |
|---|---|---|---|
| 4,818,710 A | 4/1989 | Sutherland et al. | |
| 4,922,092 A | 5/1990 | Rushbrooke et al. | |
| 4,959,301 A | 9/1990 | Weaver et al. | |
| 4,965,725 A | 10/1990 | Rutenberg | |
| 5,016,283 A | 5/1991 | Bacus et al. | |

(Continued)

FOREIGN PATENT DOCUMENTS

| | | |
|---|---|---|
| EP | 0317139 | 4/1988 |
| EP | 0468705 | 1/1992 |
| EP | 0902394 | 3/1999 |

(Continued)

OTHER PUBLICATIONS

D.L. Taylor, "The new vision of light microscopy", American Scientist 80:322-335, 1992.
K. A. Giuliano et al., "Measurement and manipulation of cytoskeletal dynamics in living cells", Current Opinion in Cell Biology 7:4-12, 1995.

(Continued)

*Primary Examiner*—Jingge Wu
*Assistant Examiner*—Abolfazl Tabatabai
(74) *Attorney, Agent, or Firm*—Beyer Weaver LLP

(57) ABSTRACT

Image analysis methods and apparatus are used for determination of the ploidy of cells. The methods may involve segmenting an image to identify one or more discrete regions occupied by cells or nuclei, determining the presence of a particular ploidy indicator feature within the region(s), and providing a value of the indicator feature to a model that classifies cells' ploidy on the basis of the indicator feature. In some embodiments, the indicator feature is a level of DNA in a cell. In certain embodiments, the method further comprises treating one or more cells with a marker that highlights the ploidy indicator feature. In certain embodiments, the cells are treated prior to producing one or more images of the one or more cells. In certain embodiments, the ploidy indicator feature comprises DNA and the marker co-locates with DNA and provides a signal that is captured in the image. In certain embodiments, the signal comprises a fluorescent emission.

32 Claims, 8 Drawing Sheets
(3 of 8 Drawing Sheet(s) Filed in Color)

U.S. PATENT DOCUMENTS

| | | | |
|---|---|---|---|
| RE34,214 | E | 4/1993 | Carlsson et al. |
| 5,281,517 | A | 1/1994 | Bacus et al. |
| 5,287,272 | A | 2/1994 | Rutenberg et al. |
| 5,326,691 | A | 7/1994 | Hozier |
| 5,355,215 | A | 10/1994 | Schroeder et al. |
| 5,526,258 | A * | 6/1996 | Bacus ................. 382/129 |
| 5,548,661 | A | 8/1996 | Price et al. |
| 5,655,028 | A | 8/1997 | Soll et al. |
| 5,710,022 | A | 1/1998 | Zhu et al. |
| 5,733,721 | A * | 3/1998 | Hemstreet et al. .......... 435/6 |
| 5,741,648 | A | 4/1998 | Hemstreet et al. |
| 5,768,412 | A | 6/1998 | Mitsuyama et al. |
| 5,776,748 | A | 7/1998 | Singhvi et al. |
| 5,777,888 | A | 7/1998 | Rine et al. |
| 5,790,692 | A | 8/1998 | Price et al. |
| 5,790,710 | A | 8/1998 | Price et al. |
| 5,804,436 | A | 9/1998 | Okun et al. |
| 5,856,665 | A | 1/1999 | Price et al. |
| 5,893,095 | A | 4/1999 | Jain et al. |
| 5,919,646 | A | 7/1999 | Okun et al. |
| 5,932,872 | A | 8/1999 | Price |
| 5,962,520 | A | 10/1999 | Smith et al. |
| 5,976,825 | A | 11/1999 | Hochman |
| 5,985,549 | A | 11/1999 | Singer et al. |
| 5,989,835 | A | 11/1999 | Dunlay et al. |
| 5,991,028 | A | 11/1999 | Cabib et al. |
| 5,995,143 | A | 11/1999 | Price et al. |
| 6,007,996 | A | 12/1999 | McNamara et al. |
| 6,008,010 | A | 12/1999 | Greenberger et al. |
| 6,078,681 | A | 6/2000 | Silver |
| 6,083,763 | A | 7/2000 | Balch |
| 6,103,479 | A | 8/2000 | Taylor |
| 6,146,830 | A | 11/2000 | Friend et al. |
| 6,169,816 | B1 | 1/2001 | Ravkin |
| 6,222,093 | B1 | 4/2001 | Marton et al. |
| 6,345,115 | B1 * | 2/2002 | Ramm et al. .............. 382/133 |
| 6,615,141 | B1 | 9/2003 | Sabry et al. |
| 6,658,143 | B2 | 12/2003 | Hansen et al. |
| 2002/0141631 | A1 | 10/2002 | Vaisberg et al. |
| 2002/0154798 | A1 | 10/2002 | Cong et al. |

FOREIGN PATENT DOCUMENTS

| | | |
|---|---|---|
| WO | WO 87/02802 | 5/1987 |
| WO | WO 93/21511 | 10/1993 |
| WO | WO94/11841 | 5/1994 |
| WO | WO 95/10036 | 4/1995 |
| WO | WO/9522749 | 8/1995 |
| WO | WO 96/01438 | 1/1996 |
| WO | WO 96/09605 | 3/1996 |
| WO | WO 97/20198 | 6/1997 |
| WO | WO 97/40055 | 10/1997 |
| WO | WO 97/43732 | 11/1997 |
| WO | WO 97/45730 | 12/1997 |
| WO | WO 98/05959 | 2/1998 |
| WO | WO 98/35256 | 8/1998 |
| WO | WO 98/38490 | 9/1998 |
| WO | WO 98/44333 | 10/1998 |
| WO | WO 98/45704 | 10/1998 |
| WO | WO 99/05323 | 2/1999 |
| WO | WO 99/08091 | 2/1999 |
| WO | WO 99/17116 | 4/1999 |
| WO | WO 99/39184 | 8/1999 |
| WO | WO 99/44062 | 9/1999 |
| WO | WO 99/54494 | 10/1999 |
| WO | WO 99/67739 | 12/1999 |
| WO | WO 00/03246 | 1/2000 |
| WO | WO 00/06774 | 2/2000 |
| WO | WO 00/17624 | 3/2000 |
| WO | WO 00/17643 | 3/2000 |
| WO | WO 00/17808 | 3/2000 |
| WO | WO 00/26408 | 5/2000 |
| WO | WO 00/29984 | 5/2000 |
| WO | WO 00/31534 | 6/2000 |
| WO | WO 00/33250 | 6/2000 |
| WO | WO 00/43820 | 7/2000 |
| WO | WO 00/49540 | 8/2000 |
| WO | WO 00/50872 | 8/2000 |
| WO | WO 00/60356 | 10/2000 |
| WO | WO 00/65472 | 11/2000 |
| WO | WO00/70528 | 11/2000 |
| WO | WO0135072 A2 | 5/2001 |

OTHER PUBLICATIONS

BioDx, Internet Archive Way-Back Machine, Feb. 4, 1997 From website www.biodx.com.

A. Waggoner et al., "Multiparameter Fluorescence imaging microscopy: re-agents and instruments" Human Pathology, vol. 27, No. 5, 494-502, 1996.

Benveniste et al., "Characterization of Internalization and endosome formation of epidermal growth factor in transfected NIH-3T3 cells by computerized image-intensified three-dimensional fluorescence microscopy", The Journal of Cell Biology 109: 2105-2115, 1989.

K.L. Carey et al., "Evidence using a green fluorescent protein-glucocorticoid receptor chimera that the RAN/TC4 GTPase mediates an essential function independent of nuclear protein import", The Journal of Cell Biology, vol. 133, No. 5, 985-996, 1996.

J. Kolega et al., "Quantitation of cytoskeletal fibers in fluorescence images: stress fiber disassembly accompanies dephosphorylation of the regulatory light chains of myosin II", Bioimaging 1:136-150, 1993.

D.L. Farkas et al., "Multimode light microscopy and the dynamics of molecules, cells, and tissues", Annu. Rev. Physiol. 55:785-817, 1993.

W. Böcker et al., Automated cell cycle analysis with fluorescent microscopy and image analysis, Phys. Med. Biol. 41:523-537, 1996.

R. Pepperkok et al., "System for quantitation of gene expression in single cells by computerized microimaging: Application to c-*fos* expression after microinjection of anti-casein kinase II antibody", Experimental Cell Research 204:278-285, 1993.

F. Hanakam, "Myristoylated and non-myristoylated forms of the pH sensor protein hisactophilin II: intracellular shuttling to plasma membrane and nucleus monitored in real time by a fusion with green fluorescent protein", The EMBO Journal 15(12):2935-43, 1996.

N.B. Cole, "Golgi Dispersal during microtubule disruption: Regeneration of Golgi stacks at Peripheral Endoplasmic Reticulum Exit sites," Molecular Biology of the Cell, vol. 7, 631-650, 1996.

B.M. Machiels Subcellualr localization of proteasomes in apoptotic lung tumor cells and persistence as compared to intermediate filaments European Journal of Cell Biology 70:250-259, 1996.

N. Yasuhara et al., "Essential Role of active nuclear transport in apoptosis" Genes to Cells 2:55-64, Jan. 1997.

BioDx, Inc., Internet archive, way back machine May 21, 1997 From website www.biodx.com.

M.V. Rogers, "Light on high -throughput screening: fluorescence-based assay technologies", Drug Discovery Today, vol. 2, No. 4, 156-160 Apr. 1997.

W. Böcker et al., "Image Processing algorithms for the automated micronucleus assay in binucleated human lymphocytes", Cytometry 19:283-294 (1995).

Lansing D. Taylor, U.S. Appl. No. 60/018,696, filed May 30, 1996.

Mattheakis et al., PCT Search Report for Int'l Application No. PCT/US2004/022970, Int'l Filing Date Jul. 15, 2004, dated Dec. 1, 2004.

Mattheakis et al., PCT Written Opinion for Int'l Application No. PCT/US2004/022970, Int'l Filing Date Jul. 15, 2004.

Towner et al., "Non-Invasive in Vivo Magnetic Resonance Imaging Assessment of Acute Aflatoxin B1 Hepatotoxicity in Rats", BBA-General Subjects, Elsevier Science Publishers, NL, vol. 1475, No. 3, Jul. 26, 2000, pp. 314-320.

Sturgeon et al., "In Vivo Assessment of Microcystin-LR-induced Hepatoxicity in the rat using proton nuclear magnetic rezsonance ($^1$H-NMR) Imaging" BBA- General Subjects, Biochemica et Biophysica Acta 1454 (1999) pp. 227-235.

Sakai et al., Rapid and Sensitive Neurotoxicity Test Based on the Morphological Changes of PC12 Cells with Simple Computer-Assisted Image Analysis, Journal of Bioscience and Bioengineering, vol. 90, No. 1, 20-24. 2000.

Hall et al., "Two Methods of Assessment of Methotrexate Hepatotoxicity in Patients with Rheumatoid Arthritis", Annals of the Rheumatic Diseases 1991, vol. 50, No. 7, pp. 471-476.

Molinari et al., "Automated Image Analysis for Monitoring Oxidative Burst in Macrophages", Analytical and Quantitative Cytology and Histology, vol. 22, No. 5, Oct. 2000, pp. 423-427.

U.S. Appl. No. 60/120,801, filed Feb. 19, 1999, Wang et al.
U.S. Appl. No. 60/142,646, filed Jul. 6, 1999, Boyce et al.
U.S. Appl. No. 60/142,375, filed Jul. 6, 1999, Boyce et al.
U.S. Appl. No. 60/108,291, filed Nov. 13, 1998, Boyce et al.
U.S. Appl. No. 60/110,643, filed Dec. 1, 1998, Smith.
U.S. Appl. No. 60/140,240, filed Jun. 21, 1999, Dunlay et al.
U.S. Appl. No. 60/127,339, filed Apr. 1, 1999, Kapur et al.
U.S. Appl. No. 60/138,119, filed Jun. 7, 1999, Adams et al.

Frank Dellaert, "The Expectation Maximization Algorithm", College of Computing, Georgia Institute of Technology, Technical Report No. GIT-GVU-02-20, Feb. 2002.

Steven S. Schreiber, "Mechanisms of Cell Death", Neurology and Anatomy & Neurobiology, Irvine Hall 114.

Uria JA, Stahle-Backdahl M, Seiki M, Fueyo A, Lopez-Otin C, "Regulation of Collagenase-3 Expression in Human Breast Carcinomas in Mediated by Stromal-Epithelial Cell Interactions", Cancer Res Nov. 1, 1997;57 (21):4882-8, Abstract.

"An Integrated Method to Determine Epithelial Transport and Bioactivity of Oral Drug Candidates *in Vitro,*" *Pharmaceutical Research*, vol. 13, No. 1, pp. 23-27, 1996.

Sunblad et al., "The use of image analysis and automation for measuring mitotic index in apical confier meristems", © Oxford University Press 1998, Journal of Experimental Botany, vol. 49, No. 327, pp. 1749-1756.

Printout from Q3DM Website (www.Q3DM.com), printed on Mar. 1, 2001, 30 Pages.

Montironi R., et al., "Computed Cell Cycle and DNA Histogram Analyses in Image Cytometry in Breast Cancer", Journal of Clinical Pathology, GB, London, vol. 46, No. 9, Sep. 1993, pp. 795-800.

Giuliano K.A., et al., "Fluorescent-Protein Biosensors: New Tools for Drug Discovery", Trends in Biotechnology, GB, Elsevier Publications, Cambridge, vol. 16, No. 3, Mar. 1998, pp. 135-140.

Printout from Automated Cell Website (www.automatedcell.com) printed on Mar. 9, 2001, 24 Pages.

Giuliano et al., "High-Content Screening: A New Approach to Easing Key Bottlenecks in the Drug Discovery *Process", J. Biomolecular Screening*, 2(4): 249 (1997).

Pauwels et al., "Determination of the Mechanism of Action of Anticancer Drugs by Means of the Computer- Assisted Microscope Image Analysis of Feulgen-Stained Nuclei", *J. Pharmacological and Toxicological Methods*. 37: 105-115 (1997).

Pauwels et al., "Monitoring Of Chemotherapy-Induced Morphonuclear Modifications By Means Of Digital Cell-Image Analysis", *I. Cancer Res. Clin. Oncol.*, 119: 533-540 (1993).

Pauwels et al., "In Vitro Digital Cell Image Analysis of Morphonuclear Modifications Induced by Natural DNA- Interacting Anticancer Drugs in Three Neoplastic Cell Lines", *Meth. Find. Exp. Clin. Pharmacol.*, 17(3): 151-161.

Pauwels et al., "The Application of Computerized Analysis of Nuclear Images and Multivariate Analysis to the Understanding of the Effects of Antineoplastic Agents and Their Mechanism of Action", *Meth. Find. Exp. Clin.* Pharmacol, 15(2): 113-124 (1993).

Pauwels et al., "Combination of Computerized Morphonuclear and Multivariate Analyses to Characterize In Vitro the Antineoplastic Effect of Alkylating Agents", J. Pharmacol. and Toxicol. Methods, 33(1): 34-45 (1995).

Weinstein et al., "An Information-Intensive Approach to the Molecular Pharmacology of Cancer", *Science*, 275: 43-349 (Jan. 17, 1997).

Cseke, I., "A Fast Segmentation Scheme for White Blood Cell Images" (1992) IEEE, pp. 530-533.

Serbouti, S., et al., "Image Segmentation and Classification Methods to Detect Leukemias", (1991) Annual Int'l Conf. of IEEE Eng. In Medicine & Biology Soc., vol. 13, No. 1, pp. 0260-0261.

Hofland et al., "Role of Tumor-Derived Fibroblasts in the Growth of Primary Cultures of Human Breast-Cancer Cells: Effects of Epidermal Growth Factor an the Somatostatin Analogue Octreotide", 1995, Int. J. Cancer: 60, 93-93.

Stearns et al., Interleukin 10 (IL-10) Inhibition of Primary Human Prostate Cell-induced Angiogenesis: IL-10 Stimulation of Tissue Inhibitor of Metalloproteinase-1 and Inhibition of Matrix Metalloproteinase (MMP)-2/MMP-9 Secretion, 1999, Clin. Can. Res. 5:189-963

Takayama et al., "Patterning cells and their environments using multiple laminar fluid flows in capillary networks", Proc. Natl., Acad. Sci. vol. 96, pp. 5545-5548, May 1999.

Hartwell et al., "Integrating Genetic Approaches into the Discovery of Anticancer Drugs". Science, vol. 278, Nov. 7, 1997, pp. 1064-1068, XP002916842.

Ng et al., "Evaluating Multi-Dimensional Indexing Structures for Images Transformed by Principal Component Analysis", Dept. of Computer Science, University of British Colombia, Vancouver, B.C. V6T 1Z4, Canada, Feb. 1, 1996, XP000642562.

Boland et al., "Automated Recognition of Patterns Characteristic of Subcellular Structures in Fluorescence Microscopy Images", Wiley-Liss, Inc., pp. 366-375, Cytometry 33:366-375 (1998).

Russ J.C., "The Image Processing Handbook," Second Edition, Boca Raton: CRC Press, 1995, pp. 169-474 and 457-461.

Lu et al., "Hierarchical Shape Recognition Using Polygon Approximation and Dynamic Alignment," IEEE Paper CH2561-9, vol. 2, pp. 976-979, 1988.

\* cited by examiner

PLOIDY CLASSIFICATION METHOD

CROSS REFERENCE TO RELATED APPLICATIONS

This application claims benefit under 35 USC § 119(e) to U.S. Provisional Patent Application No. 60/588,640, filed Jul. 15, 2004 and titled "PLOIDY ASSAY"; and this application is a continuation-in-part claiming priority under 35 USC § 120 to U.S. patent application Ser. No. 09/729,754, filed Dec. 4, 2000 now U.S. Pat. No. 6,876,760, titled CLASSIFYING CELLS BASED ON INFORMATION CONTAINED IN CELL IMAGES. This application is also related to the following US Patent documents: patent application Ser. No. 09/792,013, filed Feb. 20, 2001 (Publication No. US-2002-0154798-A1), titled EXTRACTING SHAPE INFORMATION CONTAINED IN CELL IMAGES; patent application Ser. No. 10/719,988, filed Nov. 20, 2003, titled PREDICTING HEPATOTOXICITY USING CELL BASED ASSAYS; and patent application Ser. No. 11/082,241, filed Mar. 14, 2005, titled ASSAY FOR DISTINGUISHING LIVE AND DEAD CELLS. Each of the references listed in this section is incorporated herein by reference in its entirety and for all purposes.

BACKGROUND

This invention relates to image analysis of biological cells. More specifically, it relates to methods, computer program products, and apparatus for automatically analyzing images to determine the ploidy of individual cells within those images.

A number of methods exist for investigating the effect of a treatment or a potential treatment, such as administering a pharmaceutical to an organism. Some methods investigate how a treatment affects the organism at the cellular level so as to determine the mechanism of action by which the treatment affects the organism.

One approach to assessing effects at a cellular level involves capturing images of cells that have been subject to a treatment. At times, the ploidy of individual cells within a population of cells will be part of the assessment. What are needed are image analysis techniques for determining ploidy in cells.

SUMMARY

Image analysis methods and apparatus for classifying ploidy are described herein. The methods comprise segmenting an image to identify one or more discrete regions occupied by cells or cell nuclei and determining the level of a ploidy indicator feature within the region(s). In some embodiments, the ploidy indicator feature is the total amount or mass of DNA in a cell nucleus. In certain embodiments, the method further comprises treating one or more cells with a marker that highlights the ploidy indicator feature. In certain embodiments, the cells are treated prior to producing one or more images of the one or more cells. In certain embodiments, the ploidy indicator feature comprises DNA and the marker co-locates with DNA and provides a signal that is captured in the image. In certain embodiments, the signal comprises a fluorescent emission.

In certain embodiments, a mixture model is used to determine the ploidy of individual cells in an image. In certain embodiments, the mixture model comprises multiple regions, each mapping a range of DNA mass (or a signal representing DNA mass) to a particular ploidy value. In certain embodiments, each region is represented as a gaussian distribution of DNA mass, with an associated mean and variance.

Also provided is a method of generating a model for determination of ploidy in cells. In certain embodiments, the method comprises providing a plurality of cells having a range of ploidy values; (b) imaging the plurality of cells to produce one or more images each comprising a signal corresponding to local levels of DNA in the cells; (c) analyzing the one or more images to determine an amount of DNA in at least some of the plurality of cells; and (d) fitting data representing per cell amounts of DNA determined in (c) to produce a mixture model of gaussian distributions, wherein each gaussian distribution represents a range of amounts of DNA associated with a single ploidy value. The local level of DNA refers to the amount of DNA in a cell, which is, in certain embodiments, a measure of the mass of DNA in the cell, but may also be some other quantification such as the volume of DNA in the cell, mass of DNA associated with particular features of a cells such particular histones and the like, in certain other embodiments.

In certain embodiments, the mixture model includes separate gaussian distributions (e.g., at least three separate gaussians), each representing a separate ploidy value. In certain embodiments, the, gaussian distributions included in the mixture model will have equally spaced means on a log2 scale. In certain embodiments, the cells are hepatocytes and the ploidy values include 2n, 4n, and 8n wherein n is the amount of DNA in one full set of chromosomes. In certain embodiments, model further comprises additional ploidy values such as 16n and <2n.

In certain embodiments, analyzing the images to determine amounts of DNA first comprises segmenting the images into regions representing individual nuclei or cells captured in the images. In certain embodiments, analysing the images to determine amounts of DNA further comprises determining a total intensity of the signal over the region of an image occupied by the cell or a nucleus.

Also provided is a computational method for determining the ploidy of a cell, wherein the method comprises (a) providing an image of a population of cells; (b) automatically determining an amount of DNA in at least one cell identified in the image; and (c) automatically determining the ploidy of the cell by applying the amount of DNA for that cell to a mixture model. In certain embodiments, the mixture model comprises at least two gaussian distribution of per cell DNA amount, wherein each gaussian distribution corresponds to a different ploidy value. In certain embodiments, the method will be performed on multiple cells shown in one or more images. In certain embodiments, the mixture model employed in this method represents various ploidy values, as appropriate for the specific cell types under investigation.

In certain embodiments, the amount of DNA in the cell is determined by determining the total intensity of a marker for DNA in a region of the image occupied by the cell or a nucleus of the cell. In certain embodiments, the region of an image occupied by a cell can be identified by segmenting the image.

Also provided are computer program products including machine-readable media on which are stored program instructions for implementing at least some portion of the methods described herein. Any of the methods of this invention may be represented, in whole or in part, as program instructions that can be provided on such computer readable media. Also provided are various combinations of data and data structures generated and/or used as described herein.

These and other features and advantages of the present invention will be described in more detail below with reference to the associated figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Introduction

Figure 1:
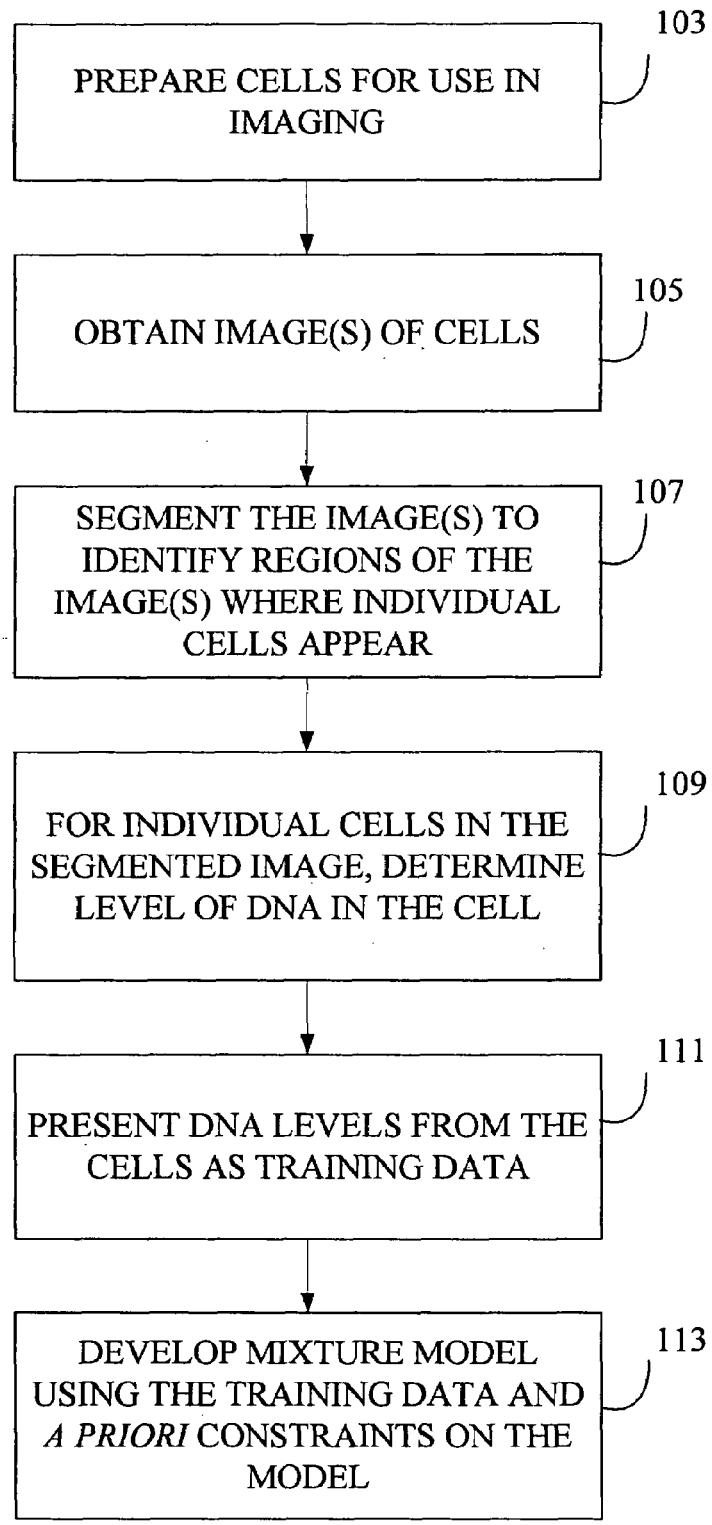
FIG. 1 is a flowchart depicting one method for producing a model that can be used to determine ploidy in accordance with an embodiment of this invention.

The present invention pertains to models (and methods of generating such models) that can be applied to images of cells and automatically determine the ploidy of one or more cells in an image. Ploidy generally refers to the number of haploid chromosome sets in a nucleus. A haploid cell has a ploidy value of 1, a diploid cell has a ploidy value of 2, etc. The models can automatically classify a cells according to their ploidy based upon the level of DNA found in cells. The local level of DNA refers to the amount of DNA in a cell, which is, in certain embodiments, a measure of the mass of DNA in the cell, but may also be some other quantification such as the volume of DNA in the cell, mass of DNA associated with particular features of a cells such particular histones and the like, in certain other embodiments.

Embodiments of the present invention employ automated image analysis techniques to identify cells in an image, determine the level of DNA in each identified cell, and based on the level of DNA, classify the ploidy of individual cells. In one embodiment, the models are "mixture models" comprised of three or more ranges of DNA level: a lower range indicating a ploidy of 2, a middle range indicating a ploidy of 4, and an upper range indicating a ploidy of 8. In certain embodiments, each range is represented as a gaussian distribution with its own mean and standard deviation. Note that the invention pertains to both methods of producing such models and methods of applying such models to images of sample cells to determine ploidy.

The term "image" is used herein in its conventional sense, but with notable extensions. For example, the concept of an image includes data representing collected light intensity and/or other characteristics such as wavelength, polarization, etc. on pixel-by-pixel basis within a defined field of view. An "image" may also include derived information such as groups of pixels deemed to belong to individual cells; e.g., as a result of segmentation. The image need not ever be visible to researchers or even displayed in a manner allowing visual inspection. Computational access to the pixel data is all that is required.

In certain embodiments, the images used as the starting point for the methods of this invention are obtained from cells that have been specially treated and/or imaged under conditions that contrast a cell's DNA from other cellular components and the background of the image. In certain embodiments, the cells are fixed and then treated with a material that binds to DNA and shows up in an image. In certain embodiments, the chosen marker specifically binds to DNA, but not to most other cellular biomolecules. The marker should provide a strong contrast to other features in a given image. To this end, the agent may be luminescent, radioactive, fluorescent, etc. Various stains and fluorescent compounds may serve this purpose. Examples of such compounds include fluorescent DNA intercalators and fluorescently labelled antibodies to DNA or other nuclear components. Examples of fluorescent DNA intercalators include DAPI Hoechst 33341, AND Ethidium homodimer-1, 7-aminoactinomycin D, Propidium iodide available from Molecular Probes, Inc. of Eugene, Oreg., or DRAQ5 from Biostatus Limited. The antibodies may be fluorescently labelled either directly or indirectly.

Note that practice of the invention is not limited to methods that treat cells with markers for DNA. Other measures of DNA presence or concentration are known and may be employed as well. In some cases, conventional imaging techniques such as phase contrast microscopy, Hoffman modulation contrast microscopy, differential interference contrast microscopy, bright field microscopy, and the like will show DNA or chromatin with sufficient contrast, at least in mitotic cells. However, marking generally improves the contrast of DNA or other marked component in images and thereby facilitates analysis of a cell or population of cells.

In certain embodiments, the marker emits a signal at an intensity related to the concentration of the cell component to which the agent is linked. For example, the local signal intensity is usually directly proportional to the local concentration of the underlying cell component. Hence, the local intensity of a DNA marker in an image may directly correspond to the local DNA concentration at particular regions within a cell. Further, the total intensity of the marker within a region occupied by a cell (in an image) may correspond to the total mass of DNA in the cell. Embodiments of this invention make use of this relationship. Ploidy correlates directly with DNA mass.

As explained below, the image analysis for determining ploidy may be used in conjunction with other image analysis techniques for identifying other relevant morphological characteristics or biological states of the cell (which states may result from treatment with a stimulus under investigation). Of course, these other morphological or biological characteristics may be more easily analyzed when cellular components exhibiting the characteristics are highlighted by marking. Examples of such components include proteins and peptides, lipids, polysaccharides, nucleic acids, etc. Sometimes, the relevant component will include a group of structurally or functionally related biomolecules such as micells or vesicles. Alternatively, the component may represent a portion of a biomolecule such as a polysaccharide group on a protein, or a particular subsequence of a nucleic acid or protein. Sub-cellular organelles and assemblies may also serve as the components (e.g., the Golgi, cell nuclei, the cytoskeleton, etc.).

As indicated, the invention may be used in research to assess the impact of a particular stimulus on a biological system (e.g., on a population of cells). The concept of a "stimulus" encompasses essentially anything that may influence the biological condition of a cell. Often the term is used synonymously with "agent" or "manipulation" or "treatment." Stimuli may be materials, radiation (including all manner of electromagnetic and particle radiation), forces (including mechanical (e.g., gravitational), electrical, magnetic, and nuclear), fields, thermal energy, and the like. General examples of materials that may be used as stimuli include organic and inorganic chemical compounds, biological materials such as nucleic acids, carbohydrates, proteins and peptides, lipids, various infectious agents, mixtures of the foregoing, and the like. Other general examples of stimuli include non-ambient temperature, non-ambient pressure, acoustic energy, electromagnetic radiation of all frequencies, the lack of a particular material (e.g., the lack of oxygen as in ischemia), temporal factors, etc.

A particularly important class of stimuli in the context of this invention is chemical compounds, including compounds that are drugs or drug candidates and compounds that are present in the environment. Related stimuli involve suppression of particular targets by siRNA or other tools for preventing or inhibiting expression. The biological impact of chemical compounds may be manifest as phenotypic changes that can be detected and characterized in accordance with embodiments of this invention.

Creating Models to Automatically Classify Ploidy

FIG. 1 presents a flowchart depicting one method for producing a model that can be used to determine ploidy in accordance with an embodiment of this invention. As shown in a block 103, the method begins by preparing the cell populations that are to be used in a data set. In some embodiments, multiple cell populations are employed to ensure that the model has broad range of applicability across multiple cell types, treatments, etc. It may also be necessary to manipulate the cells to create significant numbers of cells having the various ploidy values to be identified by the model. In certain embodiments, when preparing and imaging the test cells for the data set, one does not know exactly how many cells are in each of the multiple ploidy classifications.

In certain embodiments, one can generate different ploidy classes in a cell population by inducing a regenerative growth state; e.g., obtain hepatocytes from rat liver which is in regenerative growth state induced by partial hepatomy, or from rat during rat liver carcinogenesis. In certain embodiments, polyploidy may be induced by treatment with hormones such as EGF and insulin in vitro.

As illustrated in FIG. 1, block 105, the process obtains images of the cells that were provided in 103. The images and imaging conditions are chosen to allow extraction of relevant features that can be used to identify individual cells and characterize their ploidy. These images provide the raw data for a training set used to build the ploidy model. From the cellular images, the process extracts one or more cellular features, which allow segmentation of the image and provide a measure of the amount of DNA in each cell. In some cases, the process extracts additional features, which serve as morphological indicators of interest (e.g., Golgi or cytoskeletal features).

In order to characterize a population of cells and individual cells within an image, it is necessary to first identify the locations of the discrete cells in the image. This is the process known as segmentation. See block 107 in FIG. 1. Segmentation can be performed by various techniques including those that rely on identification of discrete nuclei and those that rely on the location of cytoplasmic proteins or cell membrane proteins. Exemplary segmentation methods are described in US Patent Publication No. US-2002-0141631-A1 of Vaisberg et al., published Oct. 3, 2002, and titled "IMAGE ANALYSIS OF THE GOLGI COMPLEX," and US Patent Publication No. US-2002-0154798-A1 of Cong et al. published Oct. 24, 2002 and titled "EXTRACTING SHAPE INFORMATION CONTAINED IN CELL IMAGES," both of which are incorporated herein by reference for all purposes.

In certain embodiments, individual nuclei are located to identify discrete cells. Any suitable stain for DNA or histones may work for this purpose (e.g., the DAPI and Hoechst stains mentioned above). Individual nuclei can be identified by performing, for example, a thresholding routine on images taken at a channel for the nuclear marker. In some embodiments, cell boundaries can be determined around each nucleus. However, in many embodiments, this is not necessary. If cell boundaries are to be determined, the cells may be treated with a non-specific marker for proteins or a marker for a cell membrane protein. In either case, a watershed algorithm has been found useful in determining boundaries of individual cells within the images. Identifying cell boundaries will facilitate identification of binuclear cells, for example.

Figure 2:
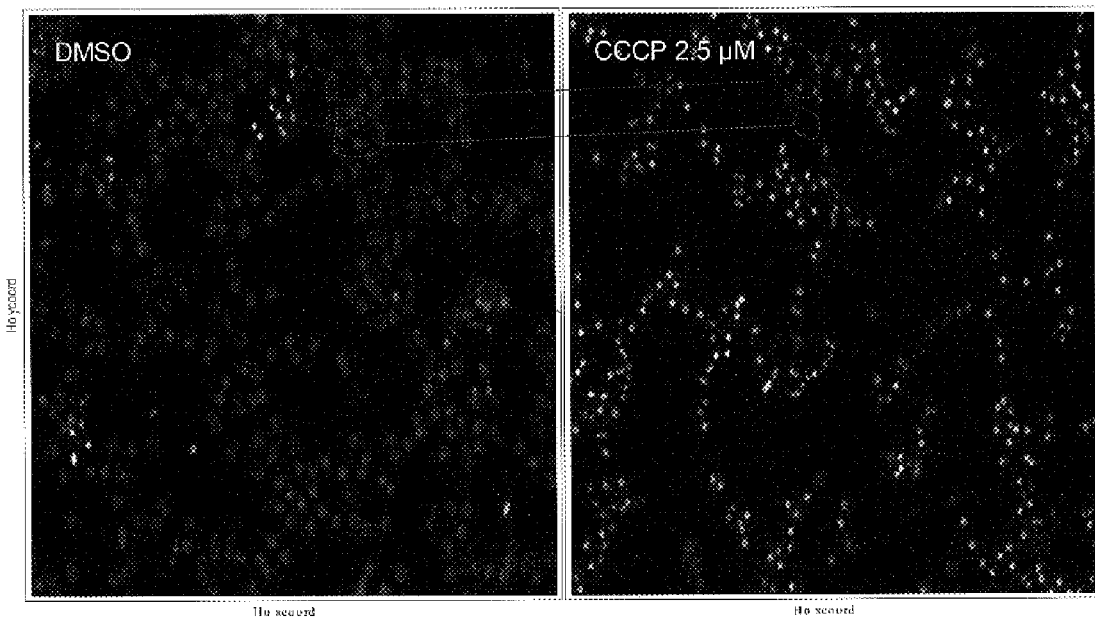
FIG. 2 presents a pair of images in which the nuclei of individual cells in two different cell populations have been identified in a segmentation procedure. A DNA stain was imaged to permit identification of the nuclei.

An exemplary segmentation process is illustrated in FIG. 2. As shown there, two images (the left one for a control population of cells treated with DMSO and the right one for a test population of cells treated with a 2.5 µM solution of the compound carbonylcyanide m-chlorophenylhydrazone (herein CCCP)) show nuclei circled in the interiors of individual cells. CCCP is a poison which acts on the cellular respiratory pathway. Cellular DNA was stained with Hoechst 33341, which emits fluorescence at a wavelength selectively collected in the FIG. 2 image to permit identification of the individual nuclei. Each such nucleus is presumed to belong to a separate cell.

After the location of each cell has been identified, the appropriate ploidy indicator feature can be extracted on a cell-by-cell basis. See block 109 of FIG. 1. As indicated above, the intensity of a marker for DNA (an indicator of local DNA concentration within the cell) can be identified for each pixel in a given cell. Each cell will be characterized on the basis of its total amount of DNA. In certain embodiments, the total amount of DNA in a cell (and specifically in the nucleus in most cases) is determined as the total intensity of the DNA marker. This value is obtained by integrating (summing) the intensity values over all the pixels in a region of an image identified by segmentation as a nucleus or cell.

After the total intensity of the DNA marker (or other indicator of DNA mass) has been produced on a per cell basis, these data are organized or made available in a form that can be used to generate a model for determining ploidy. See block 111 of FIG. 1. In a specific example, processing logic provides the DNA indicator data in the form of a histogram showing the number of cells (from the training data set) having particular levels of DNA. In other words, one axis presents various levels of DNA and the other axis presents numbers of cells. In a specific embodiment described herein, the indicator parameter of interest is the total intensity of the DNA marker in a given cell. Cells with higher values of DNA marker intensity are deemed to have higher amounts of DNA.

Figure 3A:
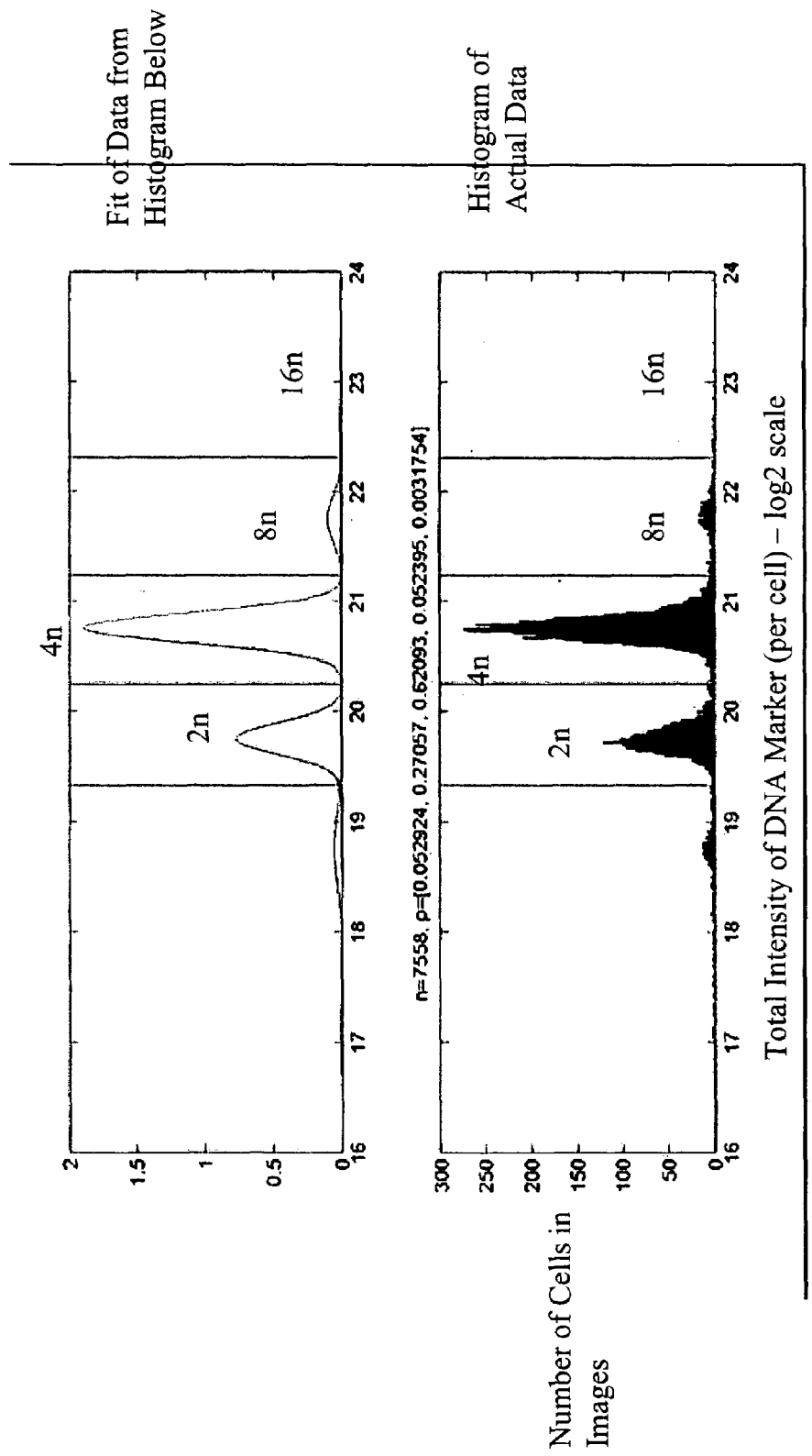
FIG. 3A is a histogram of DNA marker total intensity (per cell) taken from an image of one test population of hepatocytes. The figure also shows a mixture model of gaussian distributions fit to the data in the histogram.
Figure 3B:
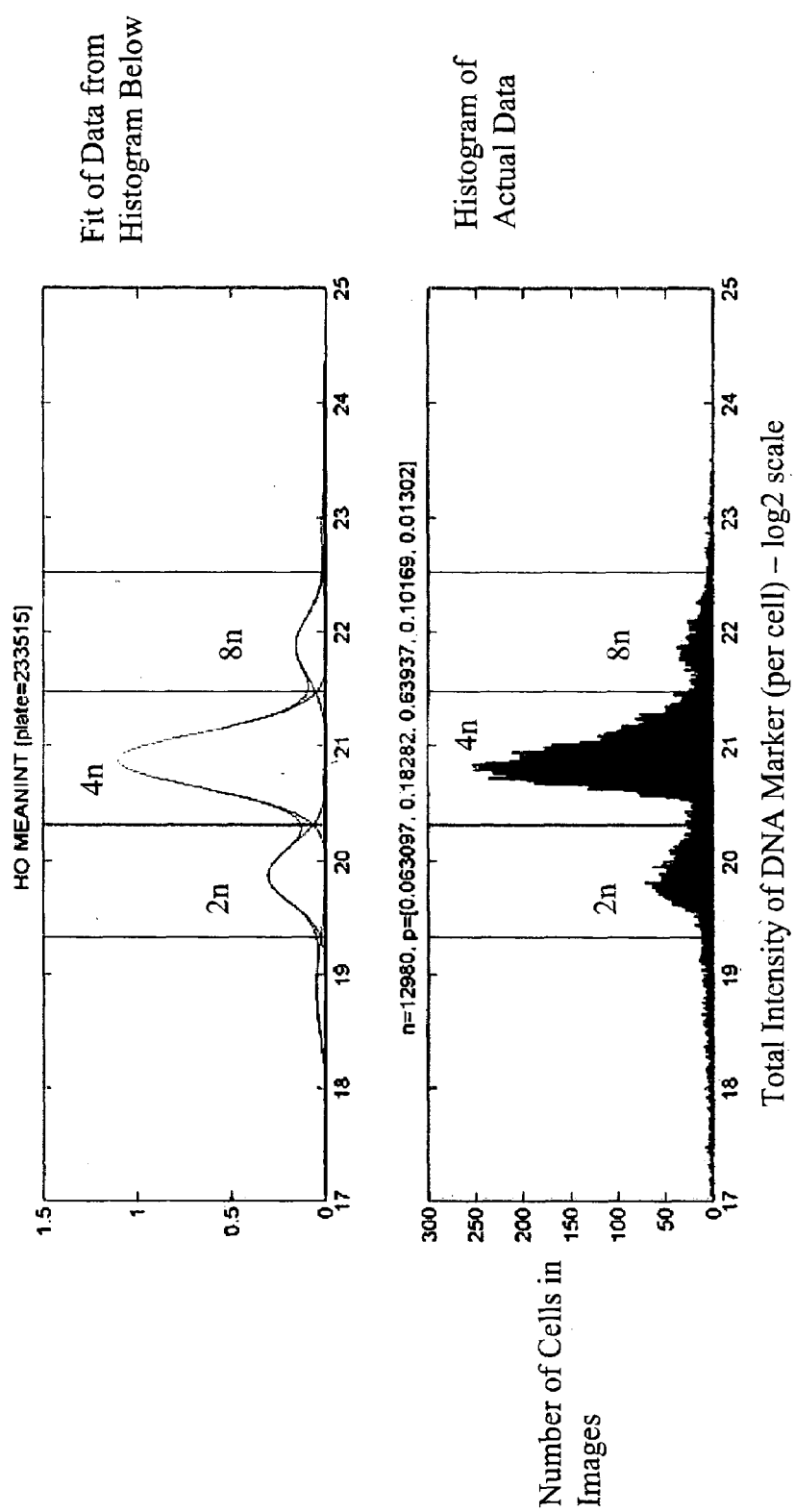
FIG. 3B is a histogram of DNA marker total intensity (per cell) taken from an image of a different test population of hepatocytes. The figure also shows a mixture model of gaussian distributions fit to the data in the histogram.

FIGS. 3A and 3B show histograms of DNA marker total intensity taken on a per cell basis. The horizontal axis shows the level of total intensity of a DNA marker, with increasingly higher values moving left to right. The vertical axis shows the number of cells found to have particular levels of the DNA marker total intensity. Histograms of the data are shown in the lower panels of both figures. Both histograms were fit to produce a mixture model of gaussian distributions, one for each different ploidy value. The test cells were hepatocytes [I am not sure what you want to say here—hepatocytes were collected from rat livers, not plates. Data were collected from multiple wells of several plates on which these hepatocytes were plated and cultured. The models resulted from fitting the data are shown in the upper panels of the figures. Because the models are essentially a "mixture" of three or more gaussian distributions they are referred to as "mixture models."

The histogram of FIG. 3A was produced using cells (hepatocytes) treated with DMSO. The total intensity of a DNA marker (Hoechst 33341) is plotted on a log2 scale (horizontal axis). As shown, most cells from the image fall into two peaks, one centered near a value of 20 and the other centered near a value of 21 (arbitrary scale). Hence the total intensity of one peak is approximately double that of the other. The histogram also shows two smaller peaks, centered near values of 19 (half the total intensity of the peak at 20) and 22 (twice the total intensity of the peak at 21). Because the means of each of the four peaks are separated from one another by approximately one unit in a log2 scale, one can conclude that each peak represents cells that have twice as much DNA as the cells in the next peak to its left (and half as much as the cells in the next peak to its right). This is what would be expected if the total intensity data accurately represented DNA mass and the imaged cell population exhibits normal ploidy.

In this case, the literature suggests that the largest peaks should belong to ploidy values of 2n, 4n, 8n, and 16n, with 4n being by far the largest. Given this constraint, the peaks were fit to three Gaussians classified as shown by the ploidy labels on the figure. See the upper panel of FIG. 3A showing a mixture model of gaussian distributions. The model was generated using a maximum likelihood estimation and the EM algorithm.

FIG. 3B shows a histogram generated from a similar data set (hepatocytes treated with DMSO) in which the cells' DNA mass distributed in different proportions over three primary ploidy classes, 2n, 4n, and 8n. Again the means of adjacent peaks were separated from one another by approximately one unit in a log2 scale, indicating reliable discrimination between ploidy classes. In this example, the proportion of cells with a ploidy of 8n is significantly increased over the case illustrated in FIG. 3A. The data shown in FIG. 3B were also fit to produce a mixture model having three gaussian distributions.

Based on the literature, hepatocyte nuclei normally have ploidy values of 2n, 4n and 8n DNA. Further, they can be binuclear. For example, two 4n nuclei in a binuclear cell will give 8n ploidy. Or a single nuclei can have 8n ploidy. In rare cases, the ploidy value is 16n (a binuclear 8n hepatocyte). Again, "n" represents the DNA in one complete set of chromosomes. See "DNA ploidy and autophagic protein degradation as determinants of hepatocellular growth and survival," P. O. Seglen, Cell Biology and Toxicology. 1997; 13: 301–15. Note that if one wishes to distinguish binuclear cells (for example when ploidy is found to be 8n), it may be necessary to segment the cells in a manner that identifies the cells' cytoplasm boundaries, as well as their nuclei. Two nuclei residing with in the bounds of a single cytoplasm will indicate a binuclear cell.

Table 1 compares hepatocyte ploidy distributions reported in the literature (Selgen) and generated from the histogram of FIG. 3A.

TABLE 1

|  | Ploidy | | | | |
| --- | --- | --- | --- | --- | --- |
|  | <2 n | 2 n | 4 n | 8 n | 16 n |
| Literature |  | 12.7% | 69.8% | 16.6% | 0.9% |
| Model | 2.2% | 21.2% | 69% | 6.9% | 0.5% |

As indicated in the table, the majority of hepatocytes have a ploidy value of 4n, with significant numbers having ploidy values of 2n and 8n. A small fraction have a ploidy of 16n. The few cells found by image analysis to have a ploidy of less than 2n are likely dead hepatocytes.

In certain embodiments, the mixture model takes the form of a heterogeneous mixture of univariate gaussians (e.g., the five gaussian distributions from the histogram shown in FIG. 3B). Each of these gaussians may be unambiguously described by the location of its mean and the value of a standard deviation. The models are deemed "heterogeneous" when the two gaussians are not constrained to have the same values of standard deviation, which is sometimes the case with models of this invention. As indicated, the mixture model assumes that the data of the training set falls into at least three distinct gaussian distributions, one for 2n ploidy, another for 4n ploidy, and a third for 8n ploidy, with some models including a fourth gaussian for 16n ploidy.

Returning to FIG. 1, the mixture model is developed using the training data and one or more a priori constraints. See block 113. In certain embodiments, this involves fitting the data associated with a histogram such as that shown in the lower panel of FIG. 3B or a similar arrangement of data. To this end, training data are provided in an appropriate format (e.g., number of cells versus level of DNA marker intensity). In addition, constraints on the mixture model (e.g., the number of gaussians and the separation of the means of those models) are provided. Such constraints are dictated by the underlying biological phenomenon being investigated. In certain embodiments, a model for classifying ploidy will be constrained to have two or more gaussians, and often three or more gaussians, as will be the case for hepatocytes. The fact that the model contains three, four, or five separate gaussians is an a priori constraint employed to ensure that the resulting model assumes the proper form. Another constraint specifies that each of the three or more means are separated from adjacent means by the same distance on a log2 scale (i.e., the separation distance between the means for 2n ploidy and 4n ploidy is equal to the separation distance between the means for 4n ploidy and 8n ploidy . . . ).

As an example, the ploidy mixture model assumes the following form:

$$\log_2(DNA\_TOTAL\_INT) \propto \sum_{i=1}^{5} \phi(\mu + (i-1), \sigma_i^2)\pi_i$$

In this expression the per cell total intensity of a DNA marker (on a log2 scale) falls into one of five Gaussians (indicated by the notation $\phi$) with an index i identifying the specific ploidy classification. For example, I=1 provides the Gaussian for ploidy 2n, i=2 provides the Gaussian for ploidy 4n, etc. Each Gaussian is characterized by a standard deviation ($\sigma_i$) and a mean (given by an integer multiple of $\mu$). The parameter $\pi_i$ indicates the proportion of cells from the image that fall into ploidy class i. Because the standard deviation, s, can vary with from Gaussian to Gaussian, the form of the model presented above is said to be "heterogenous." That form has been found to be appropriate for many ploidy applications, but the invention extends to homogeneous models as well.

In addition to providing the training data and any necessary constraints, the fitting process may require initial guesses for the various parameters defining the mixture model. Examples of the parameters in question include values of the mean and standard deviation for each gaussian in the mixture model and additionally the proportions of cells in each ploidy class (in the training set). Thus, in one example, the following information is provided with the training set: a number of separate gaussian distributions (as indicated, three or four will usually be sufficient for hepatocytes), an initial guess for the mean of each gaussian distribution, an initial guess for the standard deviation of each gaussian distribution, and an initial guess for the proportion of cells in the training set that are in each of the ploidy classes.

Note that the invention is not limited to mixtures of Gaussians. Other forms may be employed as well. Generally, however, it will characterize ploidy based on distinct ranges of total DNA mass. Further, the means or centers of the various ploidy ranges will be separated from adjacent ranges by multiples of 2 (one unit on a log2 scale). Further, the invention extends beyond the use of mixture models comprised of regions for ploidy values of 2n, 4n, and 8n (and sometimes 16n). While this distribution may be appropriate for hepatocytes and some other cell types, there will be applications where other ranges are appropriate. Some cell types, for example, form haploids. Models for these cell types will frequently have a Gaussian or other representation for ploidy=1n. Further, for aneuploid cells, it may be appropriate to include regions of DNA mass associated with non-integer multiples of n.

Note that while total intensity of the DNA marker has been identified as one embodiment for assessing DNA mass, and hence ploidy, other techniques based on an analysis of a cell's image may be employed as well. For example, it may be useful to calculate an average intensity of the pixels in a cell and then scale that value for the area of the cell image. Other techniques for determining the amount of DNA from an analysis of a cell image will be readily apparent to those having skill in the art.

Depending upon the form of the model, various types of algorithms may be employed to identify the model parameters using data from the training set. A maximum likelihood estimation using an expectation maximization (EM) algorithm is one approach. It is a well-known algorithm that is described in Dempster, A. P., Laird, N. M., and Rubin D. B., "Maximum Likelihood from Incomplete Data via the EM Algorithm," Journal of the Royal Statistical Society B, 1977 [39]: 1–38, and in McLachlan, Geoffrey J., and T. Krishnan (1997), *The EM algorithm and extensions*, John Wiley and Sons. Both of these references are incorporated herein by reference for all purposes. Other maximization techniques may be employed as well. In addition other estimation techniques can be used, such as classical constrained maximum likelihood, MiniMax estimation, and Baysian modelling with estimation using Gibbs sampling. In particular, if distributions other then Gaussian are modelled, an algorithm other than EM may be better suited. In addition to mixture models other classification methods (such as K-means) may work in some cases.

Regardless of the particular model generation algorithm employed, the resulting model may discriminate between ploidy classes using only DNA total intensity (or whatever other particular parameters are identified as providing reliable discrimination between ploidy classes). Again, the model takes the form of two or more gaussian distributions, each characterized by the position of a mean and the value of a standard deviation.

In operation, the fitting procedure assumes that the mathematical form of the model will be a mixture of Gaussians, and based on this finds a mean and a standard deviation for each Gaussian. To do this, the procedure employs the mentioned constraints (e.g., the number of peaks, the separation of these peaks, etc.). The technique converges after a few iterations of refining the estimates of the means, standard deviations, and the proportions of cells in each ploidy class. The result is a model that fits the training data well.

Using Models to Determine Ploidy

Models for discriminating between ploidy classes are used in image analysis algorithms to characterize individual cells and identify ploidy sub-populations within large groups of cells. While in certain embodiments such models are produced in accordance with the methodology described above, this need not be the case. The exact source and development of the model is not critical to this aspect of the invention.

Figure 4:
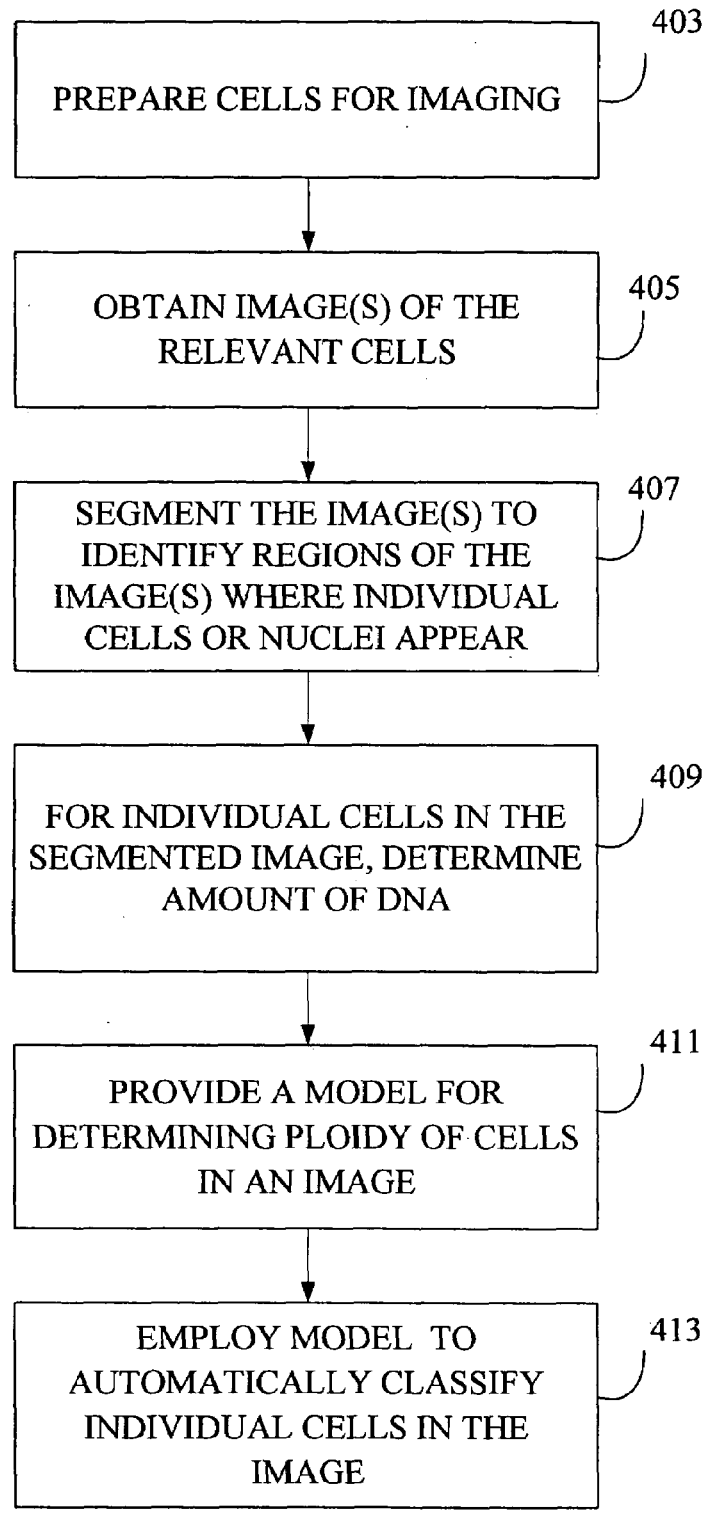
FIG. 4 is a flowchart depicting one image analysis method employing a model to determine ploidy of cells in accordance with an embodiment of this invention.

FIG. 4 is a flowchart presenting a process, in accordance with certain embodiments, for using a model for determining ploidy. In the depicted embodiment, the first four operations of the flowchart shown in FIG. 4 correspond to the first four operations presented in FIG. 1. Specifically, in FIG. 4, these operations are (1) preparing cells for analysis, (2) obtaining one or more images of the relevant cells and extracting the required features for performing the analysis, (3) segmenting the images identify regions of the images where discrete cells or cell nuclei reside, and (4) determining the amount of DNA on a cell-by-cell basis. See blocks 403, 405, 407, and 409. Note that the fourth operation (block 409) does not typically require arranging data in a histogram.

In FIG. 4, block 411, the process provides a model for determining ploidy of cells. In certain embodiments, this is a model prepared as described in the context of FIG. 1. It is important to note that many different types of models can be used, some of which are generated to be widely applicable to different cell types and different assays, and others that are specific to a very narrow range of samples. If the model is to have wide applicability, an appropriate training set spanning the conditions of interest (different cell lines, different treatment conditions, different cultures, etc.) should be provided to generate the model. Further, it should be confirmed that the model gaussians for individual ploidy classes align properly with empirical distributions for corresponding classes across all the various conditions under which the model will be applied.

In a different approach, a separate model is generated for each specific condition or assay under consideration. In one specific example, a new model is generated for each separate study, involving each separate plate. For example, a given plate may have six wells set aside to generate test samples having cells with a range of ploidy values. In this embodiment, the model is essentially generated on the fly, for each plate under consideration and applied to the other wells on the plate (i.e., the wells that were not employed to generate the model).

After the relevant model has been provided or selected, it is applied to the cells. Specifically, the model is employed to automatically classify individual cells in the image on a cell-by-cell basis. See block 413. If a mixture model is employed, as is usually the case, application of that model simply involves identifying the DNA mass (by, e.g., total intensity of a DNA marker signal) of a given cell and determining whether that value falls within the gaussian distribution for any of the ploidy classes in the model. In models comprised of a plurality of Gaussians, each having an associated mean and standard deviation, a confidence can be ascribed to the ploidy classification of a given cell based upon how close the measured intensity value comes to one of the means in the model.

Applications

As should be apparent, the invention has many different applications. In the simplest application, the invention merely determines the percentages or absolute numbers of various ploidy classes in cell samples that have been treated with particular stimuli. One extension of this basic application produces a "stimulus-response" characterization in which increasing levels of applied stimulus are employed (e.g., increasing concentration of a particular drug under investigation). The proportions of cells in various ploidy classes are then observed to change with changing levels of the stimulus. Or the selective impact of the stimulus on cells of a particular ploidy is ascertained for changing levels of stimulus. This may indicate the selective potency of the stimulus, its mechanism of action, etc. See for example, U.S. patent application Ser. No. 09/789,595, filed Feb. 20, 2001, Entitled: CHARACTERIZING BIOLOGICAL STIMULI BY RESPONSE CURVES and U.S. Provisional Patent Application No. 60/509,040, filed Jul. 18, 2003, Entitled: CHARACTERIZING BIOLOGICAL STIMULI BY RESPONSE CURVES, both of which are incorporated herein by reference for all purposes.

In some embodiments, the ploidy indicator parameter will have a separate relevance, apart from classifying cell ploidy. For example, the parameter can indicate an interesting phenotypic characteristic that helps characterize a mechanism of action, a level of toxicity, or other feature under study in conjunction with the ploidy determination. DNA and other nuclear components often present interesting morphologies or manifestations of mechanisms of action that indicate underlying cellular conditions. For example, DNA and histones show nuclear morphology at various stages of the cell cycle and can therefore be used to characterize a cell's mitotic state in some applications—in addition to characterizing the cell's ploidy. Nuclear morphology can also be employed to characterize mechanisms of cell death such as apoptosis and necrosis. See patent application Ser. No. 10/719,988, previously incorporated by reference.

In another application, the invention applies the ploidy determination to more sharply characterize an independent morphological change arising from a given stimulus. Such change may be more pronounced in cells of a particular ploidy class over others. In fact, some morphological effects might be produced in cells of only one or two ploidy classes (or might affect them in fundamentally different ways from other ploidy classes). A raw analysis of such effect on an entire population of cells without separately considering the effect on individual ploidy classes could mask the specific impact of the stimulus on cells in a ploidy class of interest.

In view of the above, the flowchart of FIG. 4 may be extended to include an additional operation in which the automated image processing extracts a feature (sometimes in addition to the ones required for segmentation and ploidy determination) from the cell images on a cell-by-cell basis. Golgi features and cytoskeletal features are examples of such additional features. In this additional operation, the image analysis algorithm determines how the additional feature is separately manifest in the individual cell ploidy populations. One example of a cellular/morphological condition that correlates with ploidy distribution is the state of growth of a tissue sample. For example, a higher percentage of 2N cells are found in actively growing livers (regenerative state or oncogenesis state) as compared to static livers.

Another application of the invention employs an image analysis method for distinguishing live cells from dead cells. In some cases, the ploidy analysis may only be relevant in live cells or in cells that have died during treatment. Thus, use of a live-dead image analysis tool in conjunction with the ploidy classification methods/tools of this invention can provide an increased level of specificity in analyzing the effects of stimuli. In certain embodiments, an image analysis method couples ploidy determination with a live-dead discrimination as well as an assay for one or more of the cellular/morphological conditions identified above. Various image analysis techniques for distinguishing live and dead cells may be employed. These techniques include those employing calcein signal, those employing signal from a cytoskeletal component such as tubulin, and various techniques known to those of skill in the art. See U.S. patent application Ser. No. 11/082,241, filed Mar. 14, 2005, and titled "ASSAY FOR DISTINGUISHING LIVE AND DEAD CELLS", which was previously incorporated by reference for all purposes.

EXAMPLES

Figure 5:
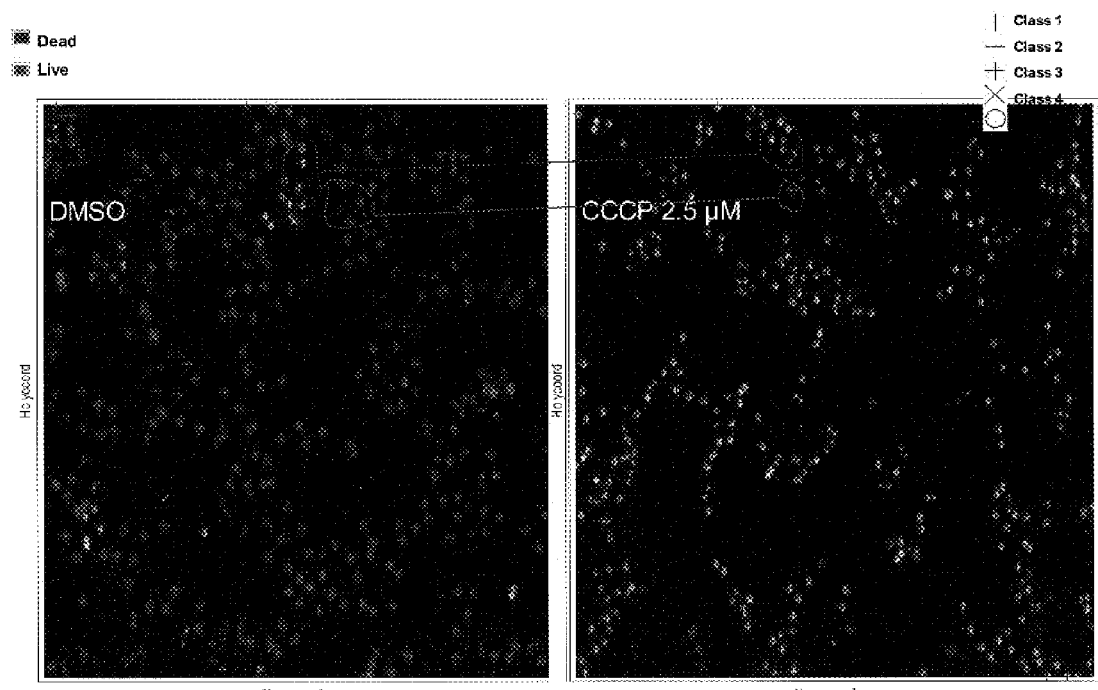
FIG. 5 presents a pair of color images, one showing control hepatocytes and the other showing hepatocytes treated with the compound CCCP. In both images, cells have been classified by ploidy using a model of this invention and have been classified as live or dead as well.

FIG. 5 shows color images of hepatocytes that have been classified into five different ploidy classes using an embodiment of the present invention. In addition, the individual hepatocytes have been classified as live or dead based on a mixture model employing mean per cell tubulin levels (as indicated by the fluorescently labeled anti-tubulin antibody DM1-$\alpha$) as an input. Lower levels of mean tubulin marker intensity indicate dead cells and higher levels indicate live cells. In the images, live cells are indicated by a green color on a superimposed symbol and dead cells are indicated by a red color on the superimposed symbol.

The left image shows cells treated with DMSO, which is non-toxic at the levels administered. The right image shows cells treated with a 2.5 $\mu$M solution of the protonophore carbonyl cyanide m-chlorophenyl hydrazone (CCCP). Not surprisingly, there is a much higher proportion of dead cells in the right image.

A ploidy model developed from the histogram in FIG. 3A was employed to classify the cells in FIG. 5. The cells were classified into five ploidy classes indicated by the following superposed symbols: <2n (|), 2n (−), 4n (+), 8n (X), and 16n (O).

Figure 6:
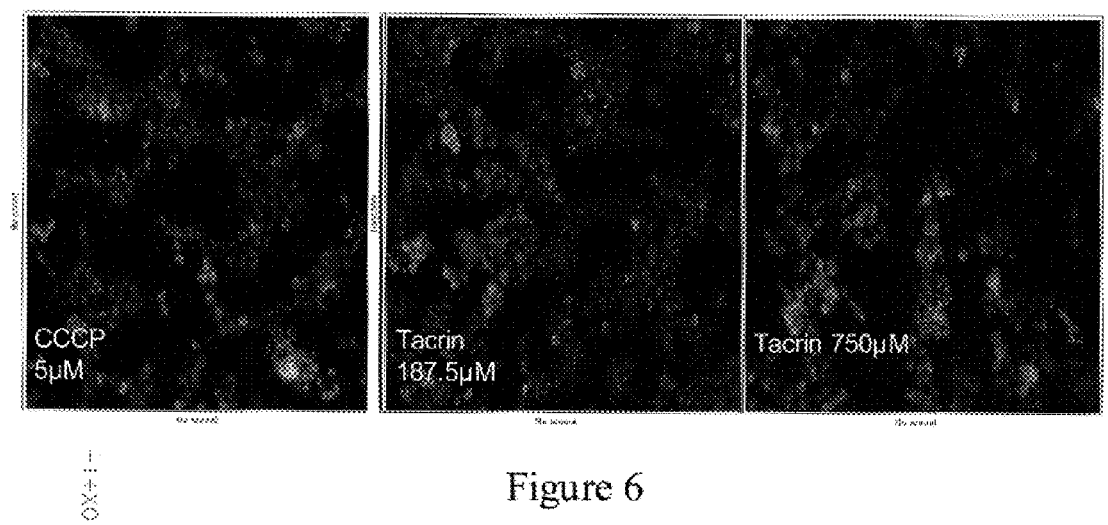
FIG. 6 is presents three images showing use of a model developed in accordance with this invention to classify cells treated with CCCP and two different concentrations of the compound Tacrin. The images also show which of the cells are live and which are dead.

FIG. 6 is presents three images showing use of a model developed in accordance with this invention to classify ploidy of cells treated with a solution of CCCP (5 μM) and two different concentrations of the compound Tacrin (187.5 μM and 750 μM). The images also show which of the cells are live and which are dead as determined using a tubulin marker and associated mixture model as in the case of FIG. 5. The hepatocytes were treated with markers for DNA (red), trans-Golgi-network (green), and tubulin (blue). As with FIG. 5, live cells are indicated by green superposed symbols and dead cells are indicated by red superposed symbols. The five ploidy classes are indicated by the symbol types employed in FIG. 5: <2n (|), 2n (−), 4n (+), 8n (X), and 16n (O).

Software/Hardware Implementation Examples

Certain embodiments of the present invention employ processes acting under control of instructions and/or data stored in or transferred through one or more computer systems. Embodiments of the present invention also relate to an apparatus for performing these operations. This apparatus may be specially designed and/or constructed for the required purposes, or it may be a general-purpose computer selectively configured by one or more computer programs and/or data structures stored in or otherwise made available to the computer. The processes presented herein are not inherently related to any particular computer or other apparatus. In particular, various general-purpose machines may be used with programs written in accordance with the teachings herein, or it may be more convenient to construct a more specialized apparatus to perform the required method steps. A particular structure for a variety of these machines is shown and described below.

In addition, embodiments of the present invention relate to computer readable media or computer program products that include program instructions and/or data (including data structures) for performing various computer-implemented operations associated with analyzing images of cells or other biological features, as well as classifying stimuli on the basis of how they impact ploidy or selectively affect cells of particular ploidy classes. Examples of computer-readable media include, but are not limited to, magnetic media such as hard disks, floppy disks, and magnetic tape; optical media such as CD-ROM disks; magneto-optical media; semiconductor memory devices, and hardware devices that are specially configured to store and perform program instructions, such as read-only memory devices (ROM) and random access memory (RAM). The data and program instructions of this invention may also be embodied on a carrier wave or other transport medium (including electronic or optically conductive pathways).

Examples of program instructions include low-level code, such as that produced by a compiler, as well as higher-level code that may be executed by the computer using an interpreter. Further, the program instructions may be machine code, source code and/or any other code that directly or indirectly controls operation of a computing machine in accordance with this invention. The code may specify input, output, calculations, conditionals, branches, iterative loops, etc.

Figure 7:
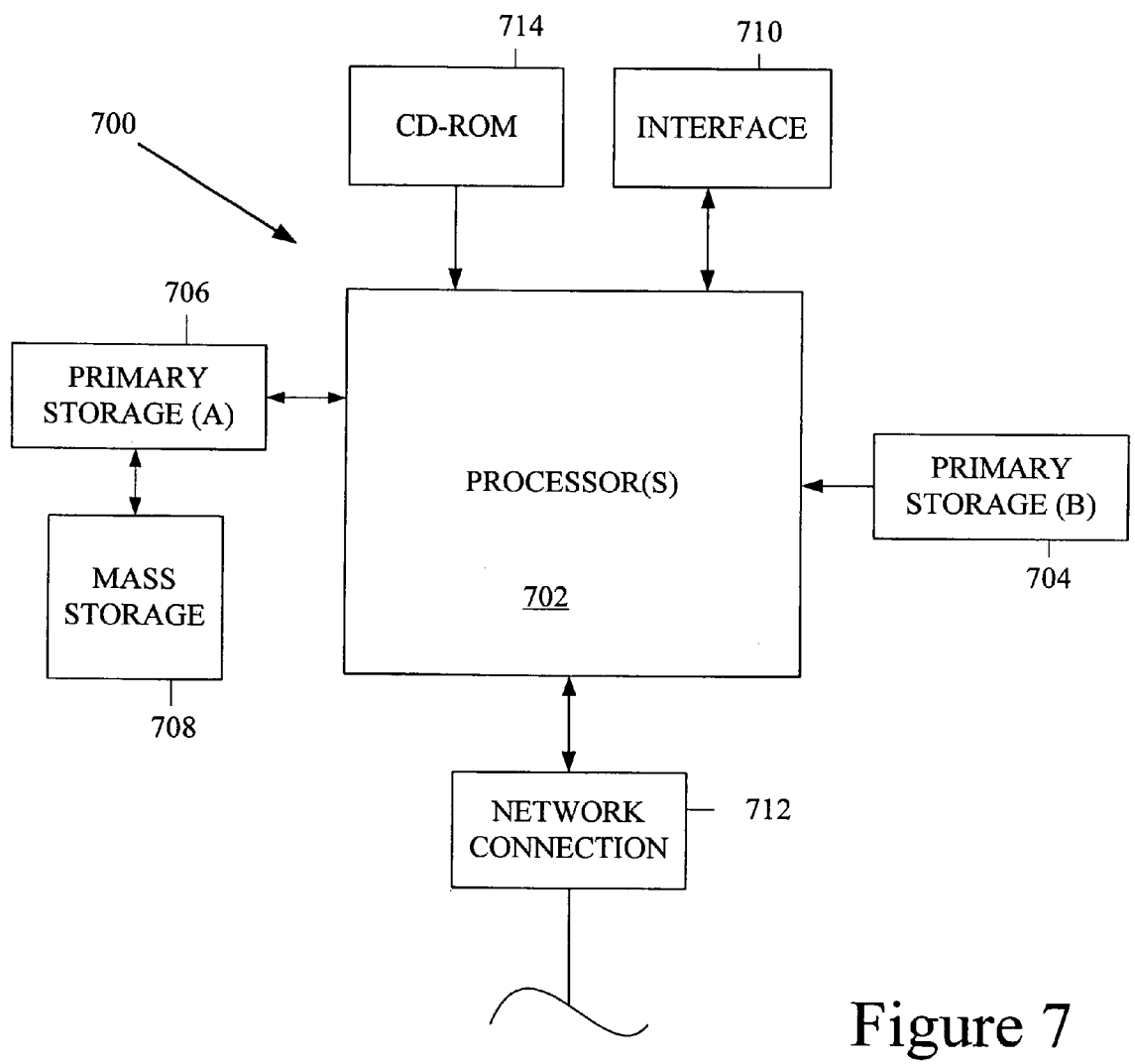
FIG. 7 is a diagrammatic representation of a computer system that can be used with the methods and apparatus of the present invention.

FIG. 7 illustrates, in simple block format, a computer system that, when appropriately configured or designed, can serve as a computational apparatus of this invention. The computer system 700 includes any number of processors 702 (also referred to as central processing units, or CPUs) that are coupled to storage devices including primary storage 706 (a random access memory, or RAM in certain embodiments), primary storage 704 (a read only memory, or ROM in certain embodiments). CPU 702 may be of various types including microcontrollers and microprocessors such as programmable devices (e.g., CPLDs and FPGAs) and non-programmable devices such as gate array ASICs or general-purpose microprocessors. In the depicted embodiment, primary storage 704 acts to transfer data and instructions uni-directionally to the CPU and primary storage 706 is used in certain embodiments to transfer data and instructions in a bi-directional manner. Both of these primary storage devices may include any suitable computer-readable media such as those described above. A mass storage device 708 is also coupled bi-directionally to primary storage 706 and provides additional data storage capacity and may include any of the computer-readable media described above. Mass storage device 708 may be used to store programs, data and the like and is typically a secondary storage medium such as a hard disk. Frequently, such programs, data and the like are temporarily copied to primary memory 706 for execution on CPU 702. It will be appreciated that the information retained within the mass storage device 708, may, in appropriate cases, be incorporated in standard fashion as part of primary storage 704. A separate mass storage device such as a CD-ROM 714 or a semiconductor storage device may also pass data uni-directionally to the CPU or primary storage.

CPU 702 is also coupled to an interface 710 that connects to one or more input/output devices such as such as video monitors, track balls, mice, keyboards, microphones, touch-sensitive displays, transducer card readers, magnetic or paper tape readers, tablets, styluses, voice or handwriting recognition peripherals, USB ports, or other well-known input devices such as, of course, other computers. Finally, CPU 702 optionally may be coupled to an external device such as a database or a computer or telecommunications network using an external connection as shown generally at 712. With such a connection, it is contemplated that the CPU might receive information from the network, or might output information to the network in the course of performing the method steps described herein.

In one embodiment, a system such as computer system 700 is used as a biological classification tool that employs cellular feature determination, thresholding, morphology characterization and/or biological classification routines for analyzing image data for biological systems. System 700 may also serve as various other tools associated with biological classification such as an image capture tool. Information and programs, including image files and other data files can be provided via a network connection 712 for downloading by a researcher. Alternatively, such information, programs and files can be provided to the researcher on a storage device.

In a specific embodiment, the computer system 700 is directly coupled to an image acquisition system such as an optical imaging system that captures images of cells or other biological features. Digital images from the image generating system are provided via interface 712 for image analysis by system 700. Alternatively, the images processed by system 700 are provided from an image storage source such as a database or other repository of cell images. Again, the images are provided via interface 712. Once in apparatus 700, a memory device such as primary storage 706 or mass storage 708 buffers or stores, at least temporarily, digital images of the cells. In addition, the memory device may store phenotypic characterizations associated with previously characterized biological conditions. The memory may also store various routines and/or programs for analyzing and presenting the data, including identifying individual cells or nuclei as well as the boundaries of such cells, characterizing the cells based on ploidy, characterizing the cells as live or dead, extracting morphological features (e.g., the shape of mitotic spindles), presenting stimulus response paths, etc. Such programs/routines may encode algorithms for characterizing intensity levels at various channels, performing thresholding and watershed analyses, integrating intensity over a region of the image such as a region occupied by a cell's nucleus, performing statistical analyses, identifying edges, characterizing the shapes of such edges, performing path comparisons (e.g., distance or similarity calculations, as well as clustering and classification operations), principal component analysis, regression analyses, and for graphical rendering of the data and biological characterizations.

OTHER EMBODIMENTS

Although the above has generally described the present invention according to specific processes and apparatus, the present invention has a much broader range of implementation and applicability. For example, while the methodology of this invention has been described in terms of DNA levels, the inventive methodology is not so limited. For example, the invention could easily be extended to other indicators found to correlate with cell ploidy. Those of ordinary skill in the art will recognize other variations, modifications, and alternatives.

What is claimed is:

1. A method of generating a model for determination of ploidy in cells, the method comprising:
   (a) providing a plurality of cells having a range of ploidy values;
   (b) imaging the plurality of cells to produce one or more images comprising a signal corresponding to local levels of DNA in the cells;
   (c) analyzing the one or more images to determine an amount of DNA in at least some of the plurality of cells; and
   (d) fitting data representing per cell amounts of DNA determined in (c) to produce a mixture model of gaussian distributions, wherein each gaussian distribution represents a range of amounts of DNA associated with a single ploidy value.

2. The method of claim 1, wherein the cell is a hepatocyte.

3. The method of claim 1, wherein the plurality of cells having a range of ploidy values is a plurality of hepatocytes having ploidy values of at least 2n, 4n, and 8n.

4. The method of claim 1 wherein the signal corresponding to local levels of DNA comprises intensity values produced by a marker for DNA.

5. The method of claim 1, wherein analyzing the one or more images comprises segmenting the one or more images into regions representing individual nuclei or cells captured in the images.

6. The method of claim 1, wherein determining an amount of DNA in a cell comprises determining a total intensity of the signal over the region of an image occupied by said cell.

7. The method of claim 1, further comprising arranging the data representing the per cell amount of DNA to produce a histogram of per cell DNA amount, where the histogram is fit to produce the mixture model.

8. The method of claim 1, wherein fitting the data produces a mixture model comprising at least three separate gaussian distributions, each representing a separate ploidy value.

9. The method of claim 8, wherein the at least three separate gaussian distributions have equally spaced means on a log2 scale.

10. The method of claim 1, wherein fitting the data produces a mixture model comprising at least two separate gaussian distributions, each representing a separate ploidy value.

11. A computer program product comprising a computer readable medium encoded with a computer program for generating a model for determining ploidy in cells, the program instructions comprising:
    (a) code analyzing one or more images of a plurality of cells to determine an amount of DNA in at least some of the plurality of cells, wherein the one or more images comprise a signal corresponding to local levels of DNA in the cells and wherein the plurality of cells have a range of ploidy values; and
    (b) code for fitting data representing per cell amounts of DNA determined in (a) to produce a mixture model of gaussian distributions, wherein each gaussian distribution represents a range of amounts of DNA associated with a single ploidy value.

12. The computer program product of claim 11, wherein the code for analyzing the one or more images comprises code for segmenting the one or more images into regions representing individual nuclei or cells captured in the images.

13. The computer program product of claim 11, wherein the code analyzing one or more images of a plurality of cells to determine an amount of DNA in at least some of the plurality of cells comprises code for determining a total intensity of the signal over the region of an image occupied by said cell.

14. The computer program product of claim 11, wherein the code for fitting data representing per cell amounts of DNA produces a mixture model comprising at least three separate gaussian distributions, each representing a separate ploidy value.

15. The computer program product of claim 14, wherein the at least three separate gaussian distributions have equally spaced means on a log2 scale.

16. The computer program product of claim 11, wherein the code for fitting the data produces a mixture model comprising at least two separate gaussian distributions, each representing a separate ploidy value.

17. A computational method of determining the ploidy of a cell, the method comprising:
    (a) providing an image of a population of cells;
    (b) automatically determining an amount of DNA in at least one cell identified in the image; and
    (c) automatically determining the ploidy of the cell by applying the amount of DNA for that cell to a mixture model comprising at least two gaussian distributions of per cell DNA amount, wherein each gaussian distribution corresponds to a different ploidy value.

18. The method of claim 17, further comprising performing (b) and (c) on multiple cells in the image.

19. The method of claim 17 wherein the image shows intensity of a marker for DNA, which was employed to treat the population of cells.

20. The method of claim 19, wherein determining the amount of DNA in the cell comprises determining the total intensity of the marker for DNA in a region of the image occupied by the cell.

21. The method of claim 17, further comprising segmenting the image to identity discrete cells at regions in the image.

22. The method of claim 21, wherein the segmenting comprises identifying discrete regions of DNA signal in the image.

23. The method of claim 17, wherein the mixture model comprises at least three gaussian distributions of per cell DNA amount, wherein each of the three gaussian distributions corresponds to a different ploidy value.

24. The method of claim 17, wherein the mixture model comprises at least four gaussian distributions of per cell DNA amount, wherein each of the four gaussian distributions corresponds to a different ploidy value.

25. The method of claim 24, wherein the ploidy values in the mixture model are 2n, 4n, 8n, and 16n, wherein n is the amount of DNA in one full set of chromosomes.

26. The method of claim 17, wherein the ploidy values in the mixture model are 2n, 4n, and 8n, and wherein is the amount of DNA in one full set of chromosomes, and wherein the cells comprise hepatocytes.

27. A computer program product comprising a computer readable medium encoded with a computer program for determining the ploidy of a cell, the program instructions comprising:
 (a) code for determining an amount of DNA in at least one cell identified in an image of a population of cells; and
 (b) code for determining the ploidy of the cell by applying the amount of DNA for that cell to a mixture model comprising at least two gaussian distributions of per cell DNA amount, wherein each gaussian distribution corresponds to a different ploidy value.

28. The computer program product of claim 27, further comprising code for performing (a) and (b) on multiple cells in the image.

29. The computer program product of claim 27, further comprising code for segmenting the image to identify discrete cells at regions in the image.

30. The computer program product of claim 29, wherein the code for segmenting comprises code for identifying discrete regions of DNA signal in the image.

31. The computer program product of claim 27, wherein the mixture model comprises at least three gaussian distributions of per cell DNA amount, wherein each of the three gaussian distributions corresponds to a different ploidy value.

32. The computer program product of claim 27, wherein the ploidy values in the mixture model are 2n, 4n, 8n, and 16n, wherein n is the amount of DNA in one full set of chromosomes.

* * * * *